United States Patent [19]

Hillenbrand et al.

[11] 4,340,629

[45] Jul. 20, 1982

[54] HIGH DENSITY INFORMATION DISC

[75] Inventors: Louis J. Hillenbrand, Columbus; Joseph R. Preston, Radnor; David A. Berry, Columbus, all of Ohio

[73] Assignee: RCA Corporation, New York, N.Y.

[21] Appl. No.: 273,241

[22] Filed: Jun. 12, 1981

[51] Int. Cl.³ ............................................. B32B 3/02
[52] U.S. Cl. .................................... 428/64; 428/167; 428/447
[58] Field of Search .......................... 428/447, 167, 64

[56] References Cited

U.S. PATENT DOCUMENTS 3,833,408  9/1974  Matthies .............................. 117/217

*Primary Examiner*—Bernard D. Pianalto
*Attorney, Agent, or Firm*—Birgit E. Morris

[57] ABSTRACT

High density information discs comprising a conductive carbon loaded polyvinylchloride disc is lubricated with a fractionated methyl alkyl siloxane lubricant which contains a quinuclidene additive.

6 Claims, No Drawings

HIGH DENSITY INFORMATION DISC

This invention relates to an improved high density information disc lubricant. More particularly, this invention relates to an improved high density information disc lubricant containing a quinuclidene additive.

BACKGROUND OF THE INVENTION

U.S. Pat. No. 3,833,408 to Matthies, herein incorporated by reference, describes the application of methyl alkyl siloxane compositions as lubricants for conductive information discs comprising a molded plastic disc having audio and video signal information in the form of geometric variations in a spiral groove. These discs are coated first with a conductive material which acts as a first electrode of a capacitor, then with a dielectric layer and a final layer of lubricant. A metallized stylus acts as a second electrode of the capacitor. The information signals are monitored by the stylus which notes changes in capacitance between the stylus and the disc surface as the information signals, in the form of a surface relief pattern, pass beneath the stylus.

Further developments in this system have produced a disc which is made of a conductive plastic material, e.g., a polyvinylchloride homopolymer or copolymer resin containing sufficient amounts of conductive carbon particles so that the disc can provide capacitance readout. The plastic resin at the surface of the disc surrounds the carbon particles to produce a dielectric surface layer. This development has eliminated the need for separate coatings of metal and a dielectric layer on the surface of the disc.

The stylus, formerly made of metallized sapphire, has also been improved so that metallized diamond can be used. Diamond is a harder, longer wearing material than sapphire but also requires improved lubrication of the disc surface.

High density information discs are also being developed which do not require a conductive surface or a grooved surface, the stylus being maintained in synchronization with the information pattern track by means of electrical signals rather than by the groove walls.

These changes in the materials used for the high density information discs and the stylus have changed the requirements for the lubricant system and improved lubricants were required. Wang et al, in copending application Ser. No. 065,065 filed Aug. 9, 1979, which is a continuation of Ser. No. 937,819 filed Aug. 29, 1978, now U.S. Pat. No. 4,275,101, have described an improved lubricant system which comprises a fractionated, purified methyl alkyl siloxane of the formula

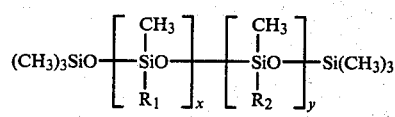

wherein $R_1$ and $R_2$ are alkyl groups of 4–20 carbon atoms, x is an integer of 2–4 and y is an integer of 0–2 and wherein the sum of x and y is 4 or less. These lubricants have improved long term stability and resistance to temperature and relative humidity changes in the atmosphere.

High density information discs of the above type are subject to a phenomenon called carrier distress. Since the polyvinylchloride composition from which the discs are made is a heavily filled, heavily lubricated and heavily plasticized composition, degradation products that are produced during molding and on storage from reactions of the disc materials and excess, incompatible additives, bleed to the surface of the disc, forming a thin layer of organic and inorganic materials. This layer interferes with playback by collecting in the grooves and by building up on the stylus. The result can be locked grooves, or dropouts of information as the disc is played. This problem has been somewhat alleviated by cleaning the discs after molding and prior to lubrication with aqueous solutions which remove at least some of the surface layer. However, with time, additional materials bleed to the surface of the disc. This bleedout can be accelerated by exposure of the disc to high temperatures, on the order of about 100° F., and high relative humidity, e.q., 90 percent and above. Lubrication of the disc has heretofore had little or no effect on reducing carrier distress. However, it would be highly desirable to be able to reduce carrier distress by means of a permanent layer on the disc surface.

SUMMARY OF THE INVENTION

We have found that when methyl alkyl siloxane lubricants are doped with compatible quinuclidene additives, the carrier distress of high density information discs, after exposure of the discs to high temperature and high relative humidity, is considerably reduced.

DETAILED DESCRIPTION OF THE INVENTION

The quinuclidenes useful in the present invention have the formula

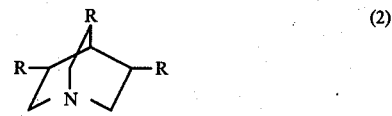

wherein R at each occurrence is an electron donating group in the position $\beta$ with respect to the nitrogen atom. Suitable electron donating groups include, for example, H, alkyl groups of 1–5 carbon atoms, $Si(CH_3)_3$, halogen and the like.

The above quinuclidenes, when added in small amounts to a methyl alkyl siloxane lubricant as described hereinabove, improve the stability of high density information discs, particularly after exposure of the disc to high temperature and high relative humidity. The exact reason for this improvement is unknown at the present time.

The amount of a quinuclidene added to the lubricant is not critical and the minimum amount that will be effective to reduce carrier distress is preferred. At the present time amounts of from about 5 to about 20 percent by weight of the methyl alkyl siloxane lubricant has been found to be satisfactory.

The quinuclidene additive described above is soluble in the methyl alkyl siloxane lubricant. The two materials can be mixed together and applied in conventional manner, as by spraying from a solvent, e.g., heptane, in which the methyl alkyl siloxane lubricant is soluble. The solvent is then evaporated, leaving a film about 200–400 angstroms thick on the surface of the disc. The two materials can also be applied to the disc surface separately but this is less desirable since it requires a separate step.

The present lubricant system, once applied, is stable with respect to atmospheric effects and provides high uniformity and reproducibility for high density information discs. In addition, this system provides excellent lubricity.

The invention will be further illustrated by the following Example but the invention is not to be limited to the details described therein. In the Example, percent is by weight unless otherwise noted.

Carrier distress time is measured by adding the amount of time in seconds (but discounting intervals of less than 10 microseconds) during disc playback when the r.f. output of the player arm is less than 150 millivolts peak to peak, and the time when the r.f. output gives above 8.6 megahertz or below 3.1 megahertz in frequency, indicating a defect. Such defects are noted by the viewer as dropouts. The present acceptable level of carrier distress for a video disc is 3 seconds in one hour of playback time.

EXAMPLE 1

A molding composition was prepared by mixing 78 parts of Geon 110×346 polyvinylchloride of the B. F. Goodrich Company; 13 parts of Ketjenblack EC carbon black of the Armak Company; 1.5 parts of dibutyltin-β-mercaptopropionate commercially available as T35 from M & T Chemical Company, Inc.; 1.0 part of Mark 275 Stabilizer of Argus Chemical Co., a dibutyltin maleate stabilizer; 2.0 parts of Acryloid K-147 and 0.75 part of Acryloid K-275, acrylic modifiers of Rohm & Haas Co.; 0.5 part of Loxiol G-30 and 0.25 part of Loxiol G-70, lubricants of Henkel International GmbH; 1.0 part of calcium stearate and 3.0 parts of diundecyl phthalate.

Video discs were compression molded from the above composition at about 360° F. (182.2° C.). A first control group of six discs was lubricated in the standard manner by spraying with the fractionated methyl alkyl siloxane as in Formula (1) above as a 0.06 percent solution in heptane.

A second group of 6 discs was lubricated with the fractionated methyl alkyl siloxane as in Formula (1) above containing 10 percent by weight of quinuclidene.

The discs were played once, then stressed by storing for one hour in a chamber maintained at 100° F. and 95 percent relative humidity and played again. The carrier distress was measured for each disc. The data, normalized to seconds of carrier distress for one hour of play, are summarized in Table I below.

TABLE I

| Group | Carrier Distress, sec./hr. | | | |
|---|---|---|---|---|
| | Initial Play | | After Stressing | |
| | Range | Median | Range | Median |
| Control | 0.0 | 0.0 | 3.4–31.6 | 15.4 |
| Example | 0.0–0.4 | 0.0 | 0.2–6.4 | 0.6 |

It is apparent the discs treated according to the invention performed better after stressing.

We claim:

1. In a high density information record adapted for use with a playback stylus to effect recovery of signals occupying a bandwidth of at least several megahertz when relative motion at a desired rate is established between said record and said stylus, said record comprising a disc of a conductive material containing an information track constituted by a surface relief pattern in said track to accommodate recovery of signals of said bandwidth upon establishment of relative motion at said rate, said record coated with a methyl alkyl siloxane lubricant having the formula

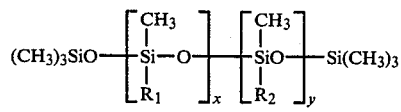

wherein $R_1$ and $R_2$ are alkyl groups of 4–20 carbon atoms, x is an integer of 2–4, y is an integer of 0–2 and wherein the sum of x plus y is 4 or less, the improvement which comprises adding to said lubricant a quinuclidene additive of the formula

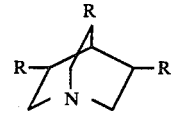

wherein R is an electron donating group.

2. A record according to claim 1 wherein x is 2–4 and y is 0.

3. A record according to claim 1 wherein R is selected from the group consisting of hydrogen, alkyl of 1–5 carbon atoms, $Si(CH_3)_3$ and halogen.

4. A record according to claim 3 wherein R at each occurrence is hydrogen.

5. A record according to claim 1 wherein from about 5 to about 20 percent by weight of the lubricant of the quinuclidene additive is present.

6. A record according to claims 1 or 4 or 5 wherein said disc is made of a conductive carbon-containing polymer or copolymer of polyvinylchloride.

* * * * *